(12) United States Patent
Seymour et al.

(10) Patent No.: US 9,008,747 B2
(45) Date of Patent: Apr. 14, 2015

(54) NEURAL INTERFACE SYSTEM WITH AN EDGE ARRAY

(75) Inventors: John Seymour, Ann Arbor, MI (US); Jamille Hetke, Brooklyn, MI (US); Rio Vetter, Ypsilanti, MI (US); Daryl Kipke, Dexter, MI (US); David Pellinen, Ann Arbor, MI (US); Kc Kong, Ann Arbor, MI (US)

(73) Assignee: NeuroNexus Technologies, Inc., Ann Arbor, MI (US)

(*) Notice: Subject to any disclaimer, the term of this patent is extended or adjusted under 35 U.S.C. 154(b) by 242 days.

(21) Appl. No.: 13/416,775

(22) Filed: Mar. 9, 2012

(65) Prior Publication Data
US 2013/0090525 A1    Apr. 11, 2013

Related U.S. Application Data

(60) Provisional application No. 61/451,083, filed on Mar. 9, 2011.

(51) Int. Cl.
| | |
|---|---|
| A61B 5/04 | (2006.01) |
| A61N 1/05 | (2006.01) |
| A61B 1/07 | (2006.01) |
| A61M 25/00 | (2006.01) |
| H05K 3/10 | (2006.01) |
| H05K 1/11 | (2006.01) |
| H05K 1/02 | (2006.01) |

(52) U.S. Cl.
CPC ............ *A61N 1/0534* (2013.01); *A61N 1/0553* (2013.01); *H05K 1/118* (2013.01); *A61B 1/07* (2013.01); *A61M 25/0023* (2013.01); *H05K 3/10* (2013.01); *H05K 1/028* (2013.01); *H05K 2201/051* (2013.01)

(58) Field of Classification Search
USPC .................................. 600/377, 378; 607/116
See application file for complete search history.

(56) References Cited

U.S. PATENT DOCUMENTS

| | | | | |
|---|---|---|---|---|
| 4,341,221 | A  * | 7/1982 | Testerman ..................... | 600/377 |
| 4,602,624 | A  * | 7/1986 | Naples et al. ................. | 607/118 |
| 5,092,332 | A  * | 3/1992 | Lee et al. ...................... | 600/377 |
| 7,054,692 | B1 * | 5/2006 | Whitehurst et al. .......... | 607/149 |
| 8,140,170 | B2 * | 3/2012 | Rezai et al. ................... | 607/116 |
| 8,195,267 | B2 * | 6/2012 | Seymour et al. .............. | 600/377 |
| 8,335,551 | B2 * | 12/2012 | Lee et al. ....................... | 600/377 |
| 2007/0191909 | A1 |  8/2007 | Ameri et al. | |
| 2008/0177363 | A1 * | 7/2008 | Schouenborg ................ | 607/116 |
| 2010/0107408 | A1 |  5/2010 | Boling | |

OTHER PUBLICATIONS

"EPSearch", 12755209, Aug. 12, 2014.

* cited by examiner

*Primary Examiner* — Lee S Cohen
(74) *Attorney, Agent, or Firm* — Michael F. Scalise

(57) ABSTRACT

The neural interface system of one embodiment includes a cylindrical shaft, a lateral extension longitudinally coupled to at least a portion of the shaft and having a thickness less than a diameter of the shaft, and an electrode array arranged on the lateral extension and radially offset from the shaft, including electrode sites that electrically interface with their surroundings. The method of one embodiment for making the neural interface system includes forming a planar polymer substrate with at least one metallization layer, patterning on at least one metallization layer an electrode array on a first end of the substrate, patterning conductive traces on at least one metallization layer, rolling a portion of the substrate toward the first end of the substrate, and securing the rolled substrate into a shaft having the first end of the substrate laterally extending from the shaft and the electrode array radially offset from the shaft.

23 Claims, 7 Drawing Sheets

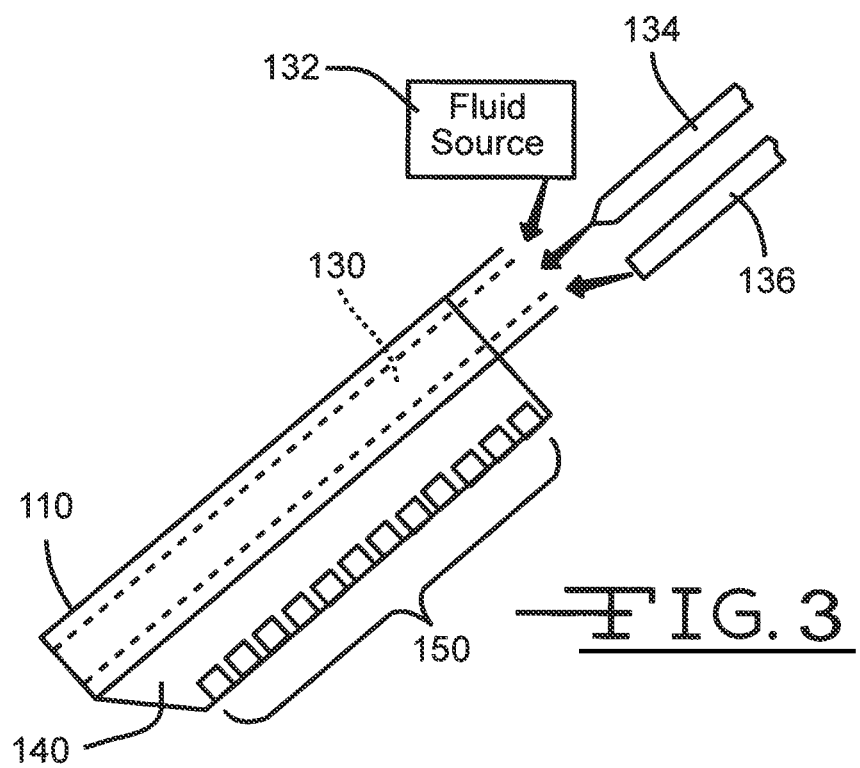
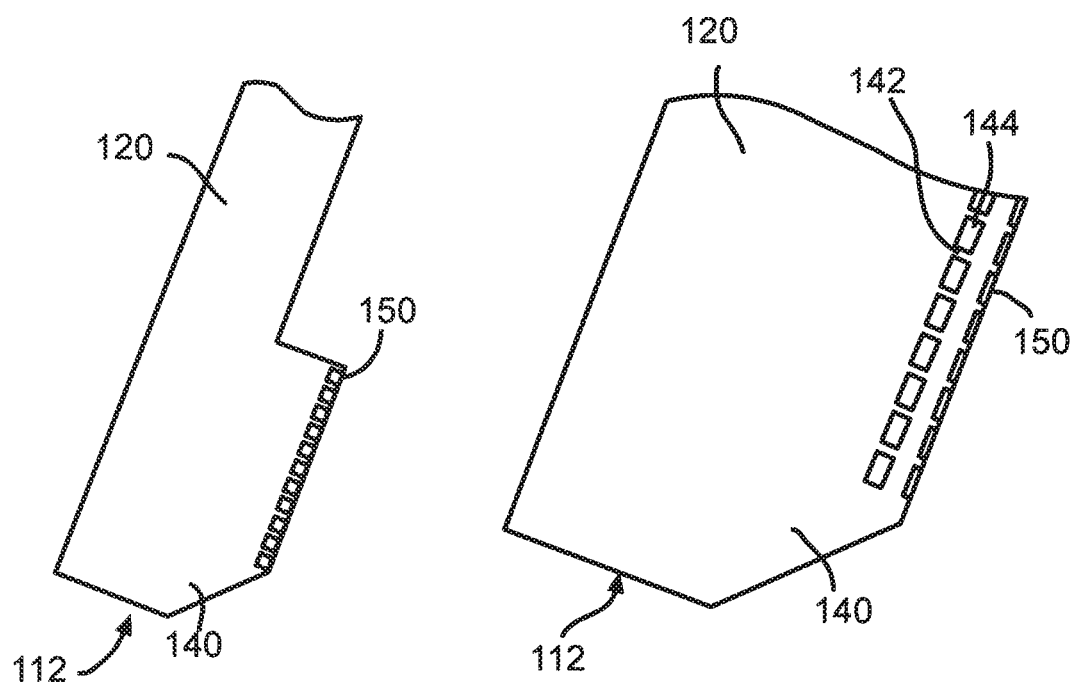

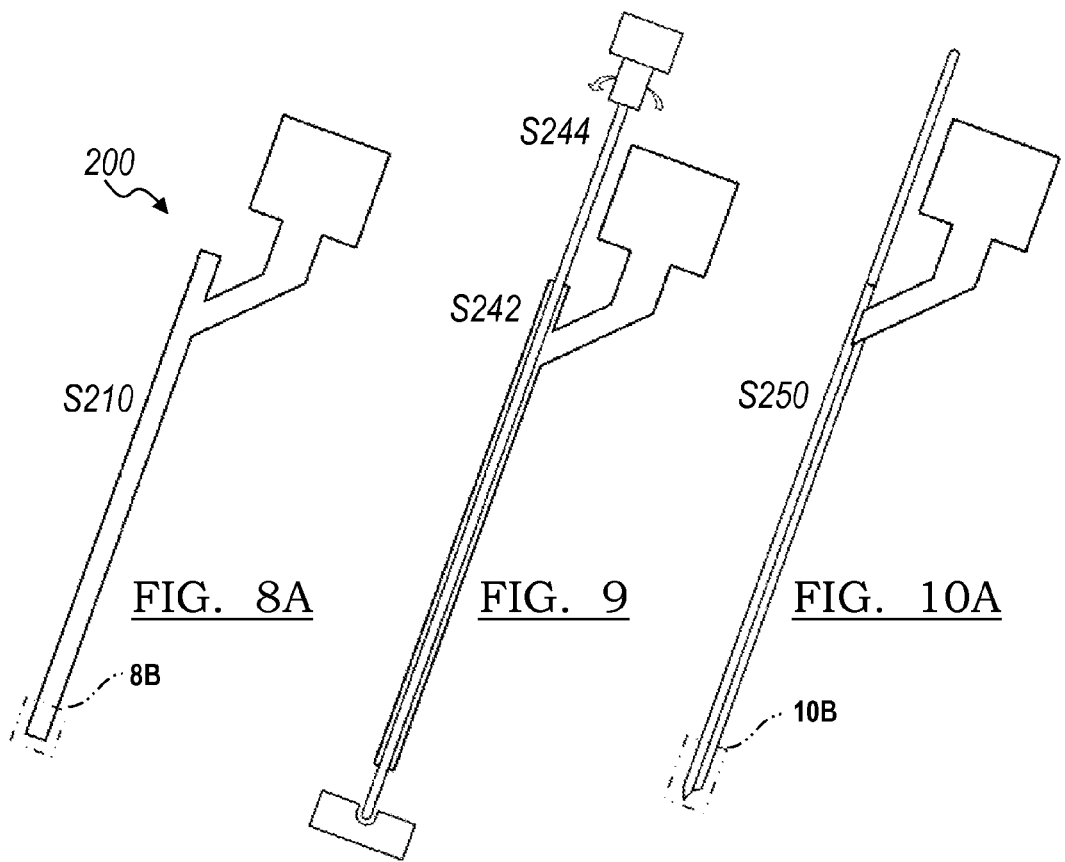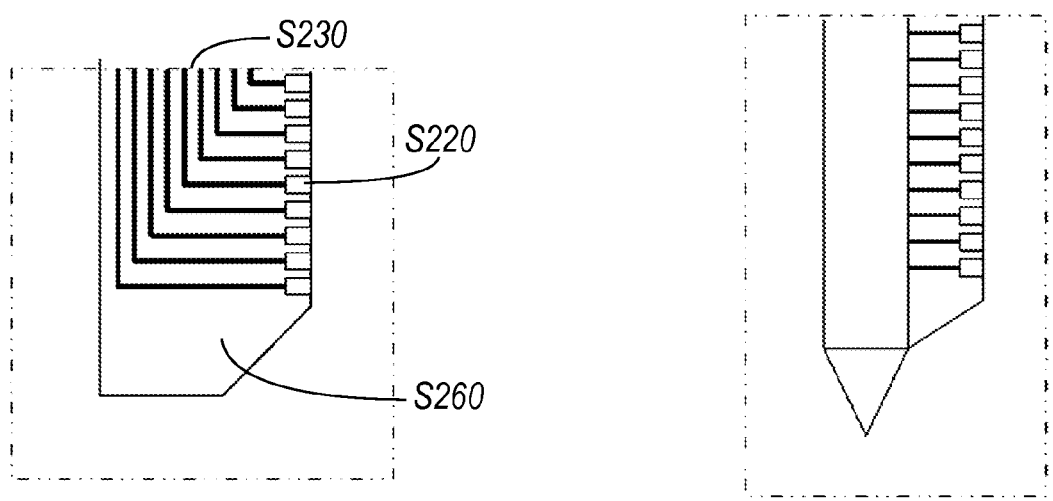

SIDE VIEW

TOP VIEW

| TABLE 2. ARBOR DAMAGE WITHIN 59-µm RADIUS |||
|---|---|---|
| TECHNOLOGY | w, µm | RANGE OF DAMAGE |
| PLANAR ARRAY | 100 | 14-40% |
| SINGLE MICROWIRE | 30 | 4-32% |
| ROLLED EDGE ARRAY | 5 | 1-8% |

US 9,008,747 B2

NEURAL INTERFACE SYSTEM WITH AN EDGE ARRAY

CROSS-REFERENCE TO RELATED APPLICATIONS

This application claims the benefit of U.S. Provisional Patent Application Ser. No. 61/451,083, entitled "Neural interface system with edge array" and filed 9 Mar. 2011, the entirety of which is incorporated herein by this reference.

TECHNICAL FIELD

This invention relates generally to the neural interface field, and more specifically to a new and useful neural interface system with an edge array in the neural interface field.

BACKGROUND

Neural interface systems are typically implantable devices that are placed into biological tissue (e.g., brain or other neural tissue) and have the ability through electrode sites, to record electrical signals from and/or electrically stimulate the tissue. Such neural interface systems may be used, for example, in treatment of neurological and psychiatric disorders. For instance, deep brain stimulation devices may provide controllable electrical stimulation of selected regions of neural tissue through strategic positioning and activation of electrode sites.

A neural interface system including a high-density array of electrode sites would be useful in many applications for exceptional control, but utilizing current conventional technology, including more electrode sites typically means a significant increase in thickness and overall size of the implantable device. Generally speaking, the larger the implantable device is, the more damage to tissue (e.g., cortical blood vessels and local tissue in and around the region of interest) the devices inflicts during implantation into the tissue. Furthermore, larger devices typically experience increased incidence of tissue encapsulation as a result of foreign body response, thereby leading to decreased electrode sensitivity.

Thus, there is a need in the neural interface field to create a new and useful neural interface system that ameliorates or eliminates the issues created by larger devices. High-channel count neural interfaces especially tend to be larger given the cost of decreasing the feature size during fabrication. This invention provides such a neural interface system, which is described in detail below in its preferred embodiments with reference to the appended drawings.

BRIEF DESCRIPTION OF THE FIGURES

FIG. 3 is a schematic of the shaft of the system of a preferred embodiment;

FIGS. 4A-4B are schematics of variations of the lateral extension of the system of a preferred embodiment;

FIGS. 7-10 are flowcharts depicting the method of a preferred embodiment and variations thereof.

DESCRIPTION OF THE PREFERRED EMBODIMENTS

The following description of preferred embodiments of the invention is not intended to limit the invention to these preferred embodiments, but rather to enable any person skilled in the art to make and use this invention.

Neural Interface System

Figure 1:
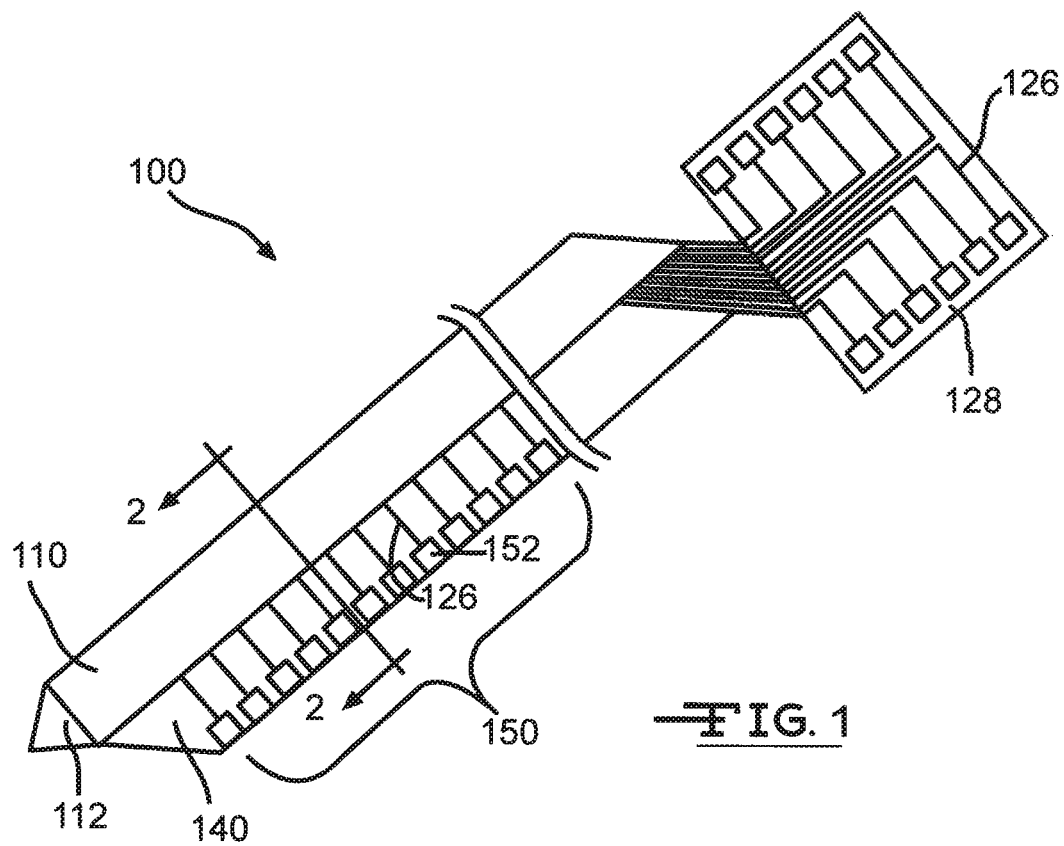
FIG. 1 is a schematic of the system of a preferred embodiment.
Figure 2:
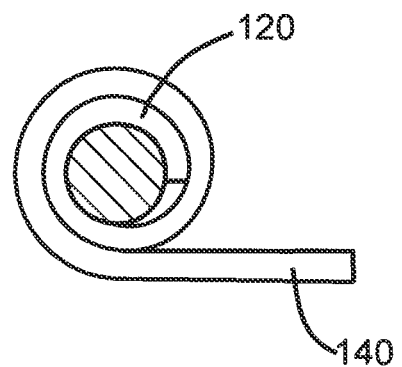
FIG. 2 is a schematic of a cross-sectional view of the shaft of the system of a preferred embodiment.

As shown in FIGS. 1 and 2, in a preferred embodiment, the neural interface system 100 of a preferred embodiment includes: a substantially cylindrical shaft 110; a lateral extension 140 longitudinally coupled to at least a portion of the shaft 110 along a longitudinal direction of the shaft 110 and having a thickness less than a diameter of the shaft 110; and an electrode array 150, at least partially arranged on the lateral extension 140 and radially offset from the shaft 110, comprising a plurality of electrode sites 152 that electrically interface with their surroundings. The neural interface system 100 of the preferred embodiment preferably provides ultra-high density, high-resolution microelectrodes on a shaft 110 implantable in tissue for electrically communicating with and interfacing with tissue, such as for recording and/or stimulation of targeted tissue. The neural interface system 100 is preferably used to interact with brain tissue or other neural tissue for research and/or clinical purposes, but additionally or alternatively can be used to interact with any suitable tissue for any suitable application. The electrode array 150 is preferably radially offset from and is smaller than the shaft 110, such that the degree of any tissue damage incurred by implantation of the shaft 110 will preferably have reduced effect on the electrode recording and/or stimulation quality and longevity. The neural interface system 100 preferably reduces local tissue damage, such as to cortical blood vessels and damage in the dendritic arbor of local neurons, such as during implantation. The neural interface system 100 preferably further reduces the occurrence of tissue encapsulation (and associated biofouling and impedance effects) around the device, which would otherwise degrade the capabilities of the neural interface system 100. Furthermore, in one preferred embodiment, the components of the neural interface system are modular, which may help to reduce costs.

The shaft 110 of the preferred neural interface system 100 preferably functions to provide structural support for the neural interface system. As shown in FIG. 2, the shaft 110 of the preferred system 100 can be configured as a rolled substrate 120. The substrate 120 is preferably a substantially planar substrate 120 that is rolled into a cylindrical shaft 110. Alternatively, the shaft 110 can be any suitable shape formed by processes other than rolling; for example, the shaft 110 can be folded into a particular shape, or the shaft 110 can include a single tube or plurality of nested tubes. The shaft 110 preferably has substantially circular cross-section taken along a radial direction, but can alternatively have an elliptical or any suitable cross-sectional shape.

In the preferred system 100, the substrate 120 includes a polymer or other suitable material that is flexible enough to be rolled or similarly manipulated. The substrate 120 preferably includes one or more metallization layers and/or one or more insulation layers interspersed between the metallization layers. As shown in FIG. 1, one or more metallization layers are preferably patterned into conductive traces 126 within the substrate 120. The metallization layers are preferably further patterned into the electrode sites 152 of the electrode array 150, as further described below. In a preferred embodiment, the substrate 120 includes at least one metallization layer, but the substrate can alternatively include any suitable number of metallization layers. The metallization layers preferably include platinum and/or iridium, but can additionally or alternatively include any suitable conductive or semi-conductive material. The insulation layers preferably include silicon carbide, but may additionally or alternatively include any suitable electrically insulating material such as silicon dioxide, silicon nitride, parylene, polyimide, LCP, and/or silicone. At least some of the layers of the substrate 120, such as the metallization layers, may be planarized by chemical-mechanical planarization or another smoothing process. Any additional suitable photolithographic processes can be performed on the substrate as desired.

As shown in FIG. 1, the substrate 120 can further include a bond pad region 128 that electrically communicates with the conductive traces 126 and/or electrode array 150, and with other circuitry and electronic devices (e.g., controller and/or signal processing devices). The bond pad region 128 is preferably on a proximal portion of the substrate 120 (with respect to the system when the system is implanted in tissue). For example, in a preferred embodiment, in an application in which the neural interface system is implanted in brain tissue, the bond pad region 128 is on or near a proximal end of the shaft 110, near or outside the surface of the brain. However, the bond pad region 128 can alternatively be located in any suitable portion of the substrate, or may be arranged in any suitable position relative to the shaft 110.

In a variation of the preferred system 100 shown in FIG. 3, the shaft 110 defines a lumen 130 within its interior space. The lumen 130 preferably passes longitudinally within the shaft 110. In some variations of the preferred system 100, the lumen 130 is centered within the shaft 110, and in some variations, the lumen 130 is offset within the shaft 110. The lumen 130 can function to deliver and/or receive substances or items in different manners in one or more different variations. In another variation of the preferred system, the lumen 130 is configured to receive and transport a fluid 132, such as for fluidic delivery of drugs or other therapeutic molecules to tissue surrounding the implanted shaft 110.

In another variation of the preferred system 100 shown in FIG. 3, the system 100 includes a stylet 134 that is insertable in the lumen 130 and preferably functions to at least provide structural support for the shaft 110 during implantation. The stylet 134 preferably includes a sharpened, pointed distal end to aid insertion into tissue and/or adjustment within tissue. In another variation of the preferred system 100, the stylet 134 includes a microwire that is insertable in the lumen 130 and preferably functions as a single channel microelectrode. In another variation of the preferred system 100, the stylet 134 functions as a mandrel, around which the substrate 120 is wrapped to form the shaft 110, as further described below.

In another variation of the preferred system 100 shown in FIG. 3, the system 100 further includes an optical light source 136 that is insertable in the lumen 130 and preferably functions to facilitate optogenetic stimulation. In particular the optical light source 136 facilitates optogenetic stimulation using optogenetic tools with light-sensitive ion channels in tissue to perturb neural circuits with cell-type specificity. The optical light source 136 is preferably an optical fiber, but may alternatively be any suitable light source. In this variation, the optical light source may operate within the neural interface system 100 similar to that described in U.S. Patent Publication No. 2011/0112591 entitled "Waveguide neural interface device", the entirety of which is incorporated herein by this reference.

Other variations of the preferred system 100 can include any other suitable substance, material, insert, and/or machine insertable within the lumen 130. Preferably, the substance or insert disposed within the lumen 130 includes a bioresorbable material that is absorbed into the surrounding tissue after a period of time. Furthermore, in some embodiments, the substance or insert disposed within the lumen 130 is permanently coupled to the shaft 110. However, in some embodiments the substance or insert disposed within the lumen 130 is temporarily coupled to the shaft 110. For example, in one embodiment, the stylet 134 is decoupled from the shaft 110 after the substrate 120 is wrapped into a shaft 110, or retracted and/or removed from the shaft 110 after the neural interface system 100 is implanted in tissue. In some embodiments, the system 100 includes multiple substances or inserts disposed within the lumen 130.

In another variation of the preferred system 100, the shaft 110 includes a pointed or sharpened distal end 112 that preferably functions to aid insertion and/or navigation of the neural interface system 100 during implantation into the tissue and/or adjustment within the tissue. For example, a distal edge of the planar substrate 120 can be shaped such that when rolled, the rolled portion of the substrate 120 forms a point on the distal end of the shaft 110. In one embodiment, at least the distal edge of the substrate 120 is reinforced to increase strength against applied loads (e.g., compression during implantation) on the distal end 112 of the shaft 110. In one embodiment, the shaft 110 includes both a pointed distal end 112 formed by the substrate 120 and a pointed (or unpointed) stylet 134 as described above.

As shown in FIGS. 4A and 4B, the system 100 can also include a lateral extension 140. The lateral extension 140 preferably functions to radially or laterally offset the electrode array 150 from the shaft 110. The lateral extension 140 is preferably longitudinally coupled to at least a portion of the shaft 110, such as along the entire length of the shaft 110, a distal portion of the shaft 110 (FIG. 4A), or any suitable portion of the shaft 110. As shown in FIG. 4A, the lateral extension 140 is preferably coupled in a continuous manner with the shaft 110. Alternatively, as shown in FIG. 4B, the lateral extension 140 can be coupled to the shaft by a series of one or more ribs bridging the lateral extension and shaft, which thereby form a perforated framework 142 between the shaft and lateral extension with openings 144.

As shown in the FIGURES, the lateral extension 140 is preferably a trailing end of the rolled substrate 120 of the shaft 110. In other words, the lateral extension 140 is preferably an unrolled portion of the substrate 120 left outside of the rolled portion of the substrate 120. For example, as shown in FIGS. 1A and 1B, the lateral extension 140 can project substantially tangentially from the shaft 110 in a roll direction of the rolled substrate of the shaft 110. In another alternative embodiment, the lateral extension 140 can be originally separate from the shaft 110, and coupled to the shaft 110 to laterally extend tangentially from the shaft 110, or extend in any suitable direction.

The lateral extension 140 preferably has a thickness that is less than the diameter of the shaft 110. Preferably, the lateral extension 140 has a subcellular thickness, such as approximately five µm thick, which preferably reduces damage to local tissue during implantation. Furthermore, reactive tissue cells are less likely to adhere to the lateral extension 140 of subcellular thickness as part of a typical foreign body response of the tissue, such that the lateral extension 140 and the electrode array 150 preferably experience a reduced amount of tissue encapsulation, which typically interferes with system operation.

As shown in the FIGURES, the preferred system 100 can also include an electrode array 150. The electrode array 150 preferably functions to electrically interface with surrounding tissue. In a preferred embodiment, the electrode array 150 is a high-density array with approximately one hundred, and more preferably at least several hundred, microelectrode sites 152. Alternatively, the electrode array 150 can include any suitable number of electrode sites. As shown in FIGS. 1A and 1B, the electrode array 150 is preferably at least partially arranged on the lateral extension 140, more preferably along a longitudinal edge of the lateral extension 140, and is radially offset from the shaft 110. The electrode array 150 preferably includes recording electrode sites and/or stimulation electrode sites that are formed in any suitable photolithographic process on the lateral extension 140. Preferably, the electrode sites 152 are formed by patterning and selectively exposing portions of the lateral extension 140 to reveal underlying metallization layers, and/or by building and patterning additional metallization layers on the lateral extension 140. However, the specific structure and formation of the electrode sites 152 may depend on the particular application of the neural interface system.

Figure 5A:
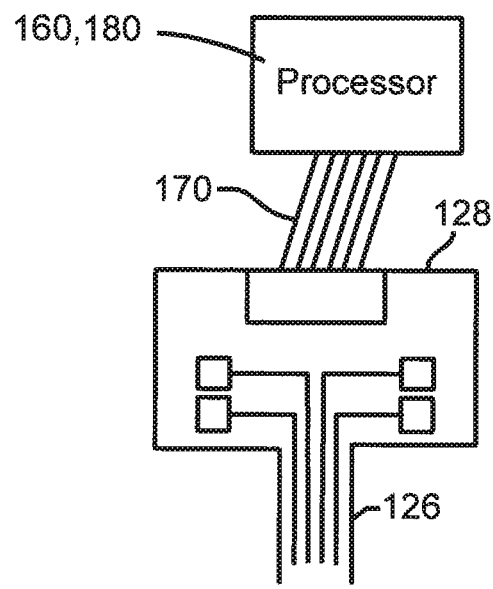
FIGS. 5A-5C are schematics of variations of electrical subsystems of the system of a preferred embodiment.
Figure 5B:
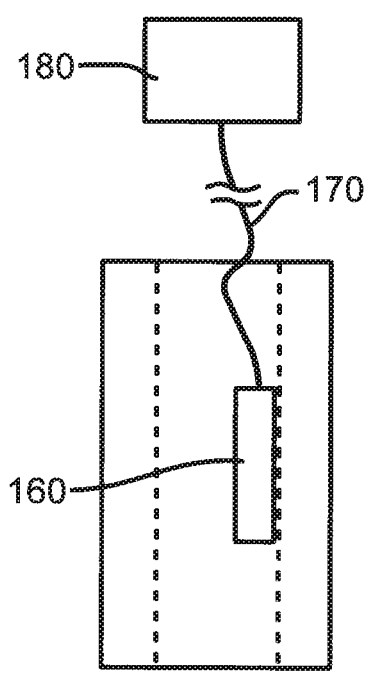
Figure 5C:
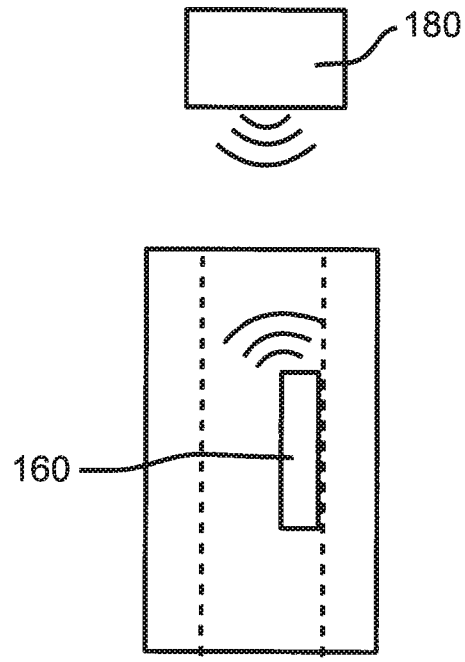

As shown in FIGS. 5A-5C, the preferred neural interface system 100 includes a first electrical subsystem 160 that functions to communicate signals to and/or from the electrode array 150 and a second electrical subsystem 180 that processes signals from the electrode array 150. The first electrical subsystem 160 preferably includes an amplifier that amplifies signals received from the electrode array 150 and transmits amplified signals to the second electrical subsystem 180. The first electrical subsystem 160 preferably further includes a multiplexer that multiplexes neural signals to and/or from the electrode array 150, thereby enabling the neural interface system 100 to include fewer conductive traces than would otherwise be required. The second electrical subsystem 180 is preferably in communication with the first electrical subsystem 160, and preferably includes a signal processor, controller, and/or any suitable electronics.

As shown in FIG. 5A, in one preferred embodiment, the first electrical subsystem 160 and/or second electrical subsystem 180 are coupled to a proximal region of the substrate 120 of the shaft 110. As shown, the conductive traces 126 preferably pass along the shaft generally in a longitudinal direction toward the bond pad region 128 or other proximal region of the substrate 120. Electrical signals are preferably communicated between the conductive traces 126 and the first electrical subsystem 160 and/or second electrical subsystem 180 through the bond pad region 128 and a hardwire connector 170 (e.g., a ribbon cable). However, the signals can additionally or alternatively be communicated with a wireless transmitter.

In another variation of the preferred system 100 shown in FIGS. 5S and 5C, at least the first electrical subsystem 160 is disposed within the lumen 130 of the shaft 110. At least a portion of the conductive traces 126 preferably extend radially inward toward the lumen 130 and are coupled to the first electrical subsystem 160 within the lumen 130. In another variation of the preferred system 100, the conductive traces 126 pass approximately circumferentially around the shaft 110 within the substrate 120, spiraling and approaching radially inward. The first electrical subsystem 160 (and/or any other electrical components) within the lumen 130 is preferably coupled to the second electrical subsystem 180 or other suitable components positioned external to the shaft) through the lumen 130, such as on or within the substrate 120, through a hardwired connection 170 (FIG. 5B), or through a wireless connection (FIG. 5C). In an alternative embodiment, both the first and second electrical subsystems 160, 180 can be disposed within the lumen.

Although omitted for clarity, the preferred embodiments of the system 100 include every combination of the variations of the shaft 110, lateral extension 140, electrode array 150, electrical subsystems 160, 180, and other components described herein. The preferred embodiments of the system 100 also include every combination of the stylet 134 or other inserts into the lumen 130 of the shaft 110, including none, one, or a plurality of such inserts into the lumen 130 of the shaft 110 as described above.

Method of Making a Neural Interface System

Figure 6:
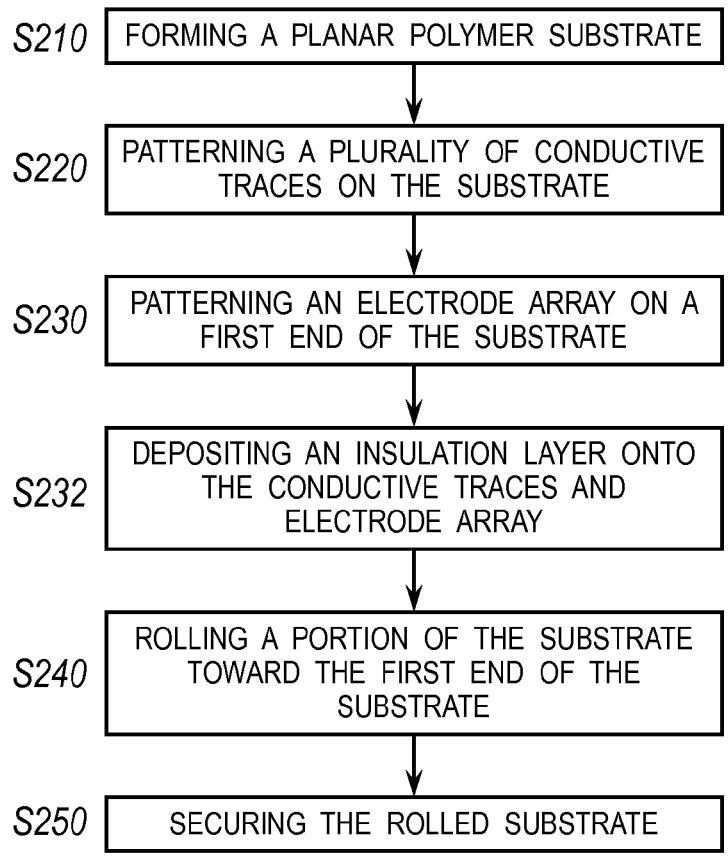

As shown in FIG. 6, a preferred method 200 of making a neural interface system includes: forming a planar polymer substrate in block S210; patterning a plurality of conductive traces in block S220, patterning an electrode array on a first end of the substrate in block S230, rolling a portion of the substrate towards the first end of the substrate in block S240, and in block S250, securing the rolled substrate into a shaft. The shaft preferably has the first end of the substrate laterally extending from the shaft and the electrode array radially offset from the shaft.

Figure 7:
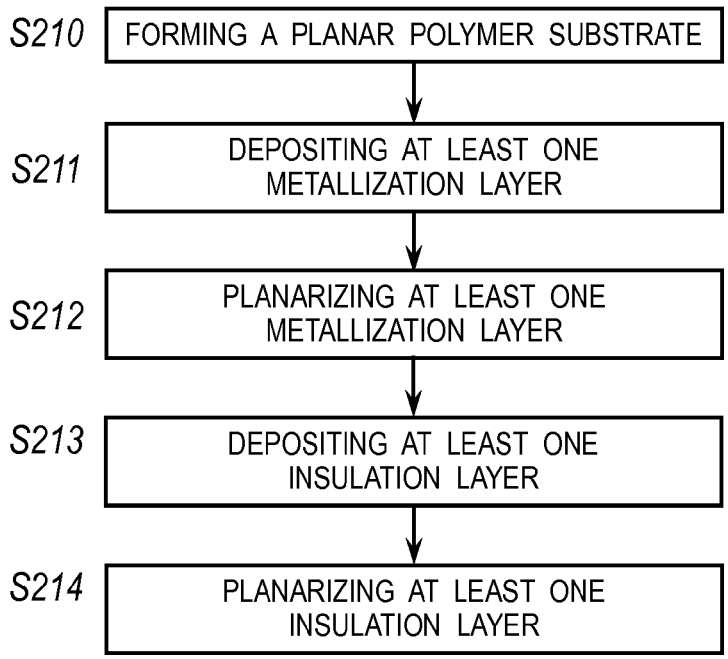

As shown in FIG. 6, block S210 recites forming a planar polymer substrate. Forming a planar polymer substrate preferably functions to prepare a structure from which the shaft, lateral extension, conductive traces, and/or electrode array is formed. In a preferred embodiment, block S210 includes depositing a plurality of metallization layers and depositing a plurality of insulation layers interspersed between the metallization layers. However, any suitable number of metallization layers and/or insulation layers can be deposited. Any suitable deposition technique or process (e.g., chemical vapor deposition) can be used. The metallization layers can be any suitable conductive material, such as platinum or iridium or gold, including appropriate metal adhesion layers. In a preferred embodiment, the insulation layers are silicon carbide, but may alternatively be any suitable insulating material. In some embodiments, the metallization layers and insulation layers are of near equal thickness, but in other embodiments at least some of the metallization layers and/or insulation layers may be of different thicknesses. As shown in FIG. 7, one variation of the preferred method can include depositing at least one metallization layer in block S211, planarizing at least one metallization layer in block S212, depositing at least one insulation layer in block S213, and/or planarizing at least one insulation layer in block S214. Planarizing preferably involves chemical-mechanical planarization, but the preferred method may additionally or alternatively include any suitable smoothing process. As shown in FIG. 6, block S220 recites patterning an electrode array on a first end of the substrate, and block S230 recites patterning a plurality of conductive traces.

As shown in FIGS. 8A and 8B, the electrode array and conductive traces are preferably patterned on one or more metallization layers of the substrate. Blocks S220 and S230 preferably function to form a plurality of electrode sites configured to interface with tissue, and a plurality of conductive traces configured to carry signals to and from the electrode sites. Blocks S220 and S230 can include any suitable photolithographic processes (e.g., masking, patterning, etching). Another variation of the preferred the method further includes forming a bond pad region on the substrate that is configured to communicate with electrical subsystems and the conductive traces and/or electrode array.

As shown in FIG. 6, the method preferably includes block S232, which recites depositing an insulation layer onto the conductive traces and electrode array. Similar to block S210, the insulation layer can include silicon carbide, but may alternatively include suitable insulating material, and can be deposited in any suitable manner. Furthermore, any suitable number of insulation layers can be deposited.

As shown in FIG. 6, block S240 recites rolling a portion of the substrate toward the first end of the substrate. Block S240 preferably functions to form a shaft of the neural interface device. As shown in FIG. 9, in a preferred embodiment, the method includes block S242, which recites coupling an insert to a second end of the substrate. The preferred method can further include block S244, which recites rolling the portion of the substrate around the insert from the second end toward the first end. The insert is preferably an elongated insert, and more preferably includes a stylet such as a microwire, an optical fiber, or any suitable insert configured to serve as a mandrel around which the shaft is formed. The insert is preferably coupled to the unrolled substrate by any suitable fastening mechanism, such as tacking with a biocompatible epoxy or another adhesive. In a preferred embodiment, the method includes coupling the insert to a rotational actuator and rolling the portion of the substrate around the insert with the rotational actuator. The rotational actuator is preferably a stepper motor, but may be a servomotor, crank, or any suitable actuator. The actuator is preferably programmed to roll a predetermined portion of the substrate (e.g., to include up to a predetermined length of the substrate in the rolled shaft), thereby leaving a portion of the substrate outside of the rolled shaft. In this embodiment, a first end of the insert is preferably coupled (e.g., with a shaft coupler) to the rotational actuator and a second end of the insert opposite the first end may be mounted to a fixture to help stabilize the insert as the substrate is rolled. After the substrate is rolled, the insert is preferably decoupled from the actuator such that the shaft of the neural interface device is independent and separate from the actuator.

As shown in FIGS. 6 and 10A-10B, block S250 recites securing the rolled substrate into a shaft. The shaft preferably has a lateral extension with the electrode array radially offset from the shaft. In a first variation, securing the rolled substrate includes applying a biocompatible epoxy or other adhesive between at least two rolled layers of the shaft. In a second variation, securing the rolled substrate includes applying a biocompatible epoxy or other adhesive on a proximal and/or distal end face of the shaft.

The preferred method can further include forming a sharpened distal end on the shaft in block S260. Block S260 functions to configure the shaft for insertion into tissue and/or adjustment within tissue. In a preferred variation, as shown in FIG. 8B, block S260 includes forming the substrate with at least one slanted edge. In this variation, the slanted edge is formed into sharpened edge or point when the substrate is rolled. In an alternative variation, block S260 includes machining a sharpened edge or point onto the substrate after the shaft is rolled. The preferred method can further include reinforcing the distal end of the shaft to better bear load, such as with a hardening treatment (e.g., chemical, treatment) of the substrate material, forming the substrate to have a thicker and/or stronger material at a distal end, and/or coupling a reinforcing material to the distal end of the substrate and/or shaft.

Although omitted for clarity, the preferred embodiments of the method includes every combination and permutation of the processes described herein. It should be understood that any of the foregoing processes and/or blocks can be performed by any suitable device, in any suitable order, in a serial or parallel manner.

Example Implementation of the Preferred System and Method

The following example implementation of the preferred system and method is for illustrative purposes only, and should not be construed as definitive or limiting of the scope of the claimed invention. In one example, the shaft includes a polymer substrate having three metallization layers that are approximately 0.7 µm, 1.0 µm, and 1.3 µm thick. The metallization layers are interspersed with silicon carbide insulation layers. A trailing end of the substrate is patterned with photolithographic processes to form a high-density electrode array including approximately 670 microelectrode sites. When the substrate is unrolled, at least a portion of the planar substrate has a width of approximately 450 µm and a thickness of approximately 5 µm. A microwire having a diameter of approximately 80 µm is tacked onto an end of the planar substrate opposite the trailing end, and the planar substrate is rolled or wrapped around the microwire, toward the trailing end, to form a shaft approximately 10 mm long and having a lateral extension projecting tangentially from the shaft. The high-density electrode array is arranged along the edge of the lateral extension such that the electrode array is radially offset from the rolled shaft.

Figure 11A:
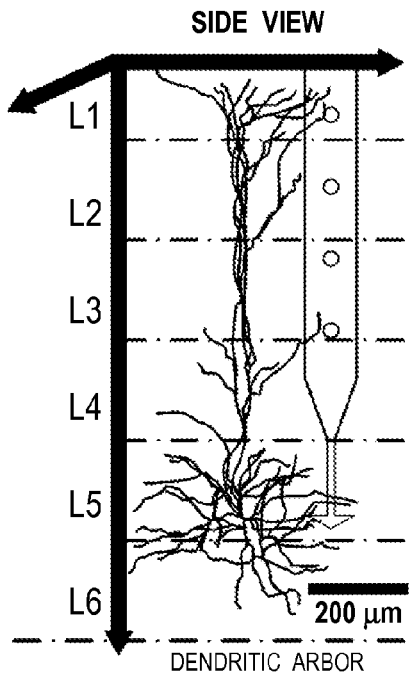
FIGS. 11A-11E are schematics comparing tissue damage imparted by an exemplary neural interface system of a preferred embodiment to tissue damage imparted by conventional planar and microwire neural devices.
Figure 11B:
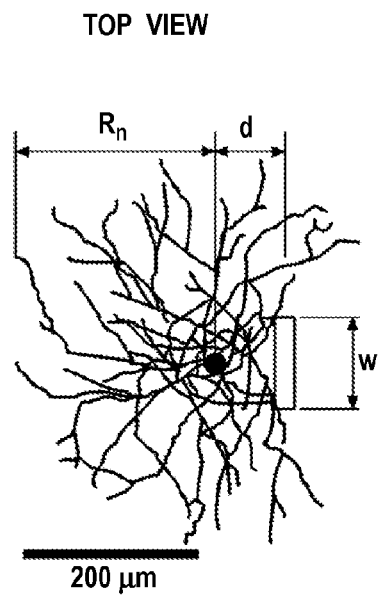
Figure 11C:
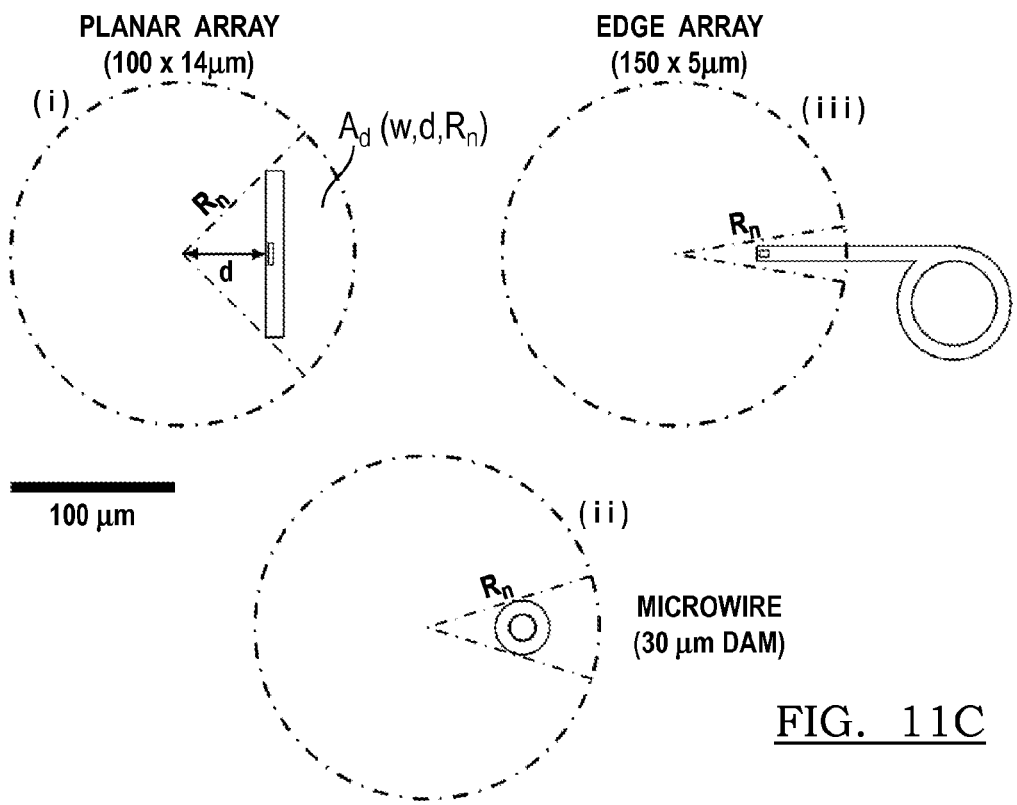
Figures 11D, 11E:
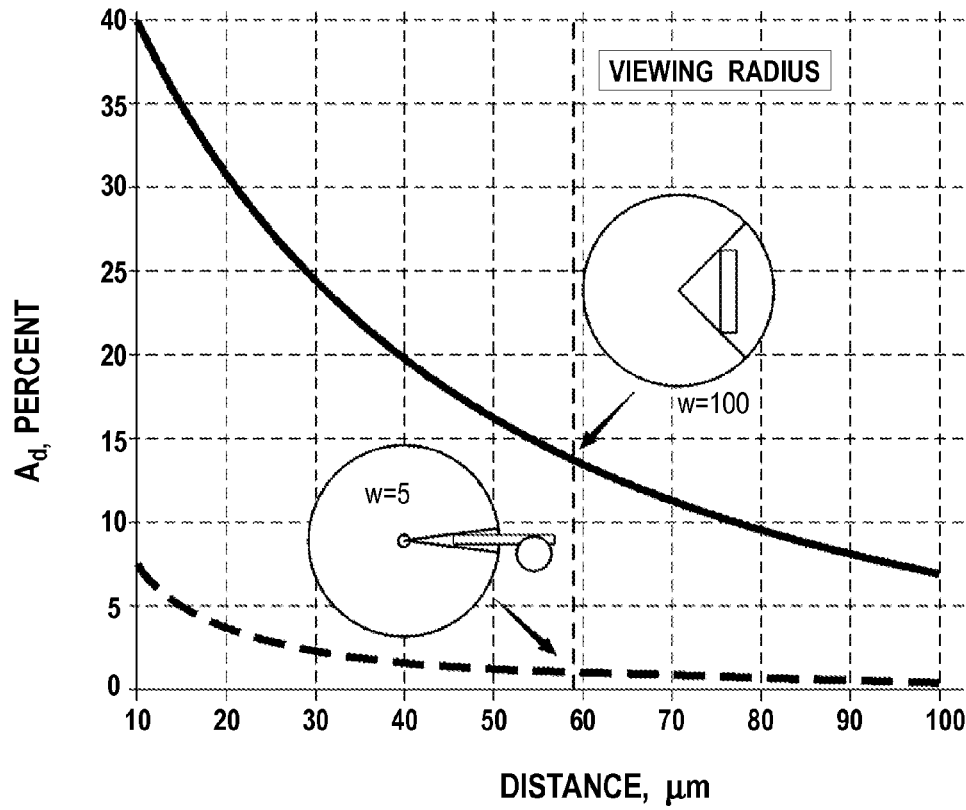

The neural interface system is preferably strategically implanted to minimize damage to a target region of interest in the tissue, especially compared to conventional planar and microwire neural devices. As shown in FIGS. 11A and 11B, a planar neural device can sever portions of a neuron during implantation, and/or can be forced to record and/or stimulate tissue further from a desired target region in order to avoid excessive damage to the target region. As shown in the schematics of FIG. 11C, an exemplary planar neural device with a width of approximately 100 µm (i) and an exemplary microwire neural device with a diameter of approximately 30 µm (ii) are estimated to result in a larger area of damage ($A_d$) to a desired target region due to their larger footprint area or "effective width" in the target region, compared to the neural interface system with an edge array with an effective width of 5 µm (iii). The shaft of the neural interface system is preferably positioned relatively distant from the target region, while the edge electrode array on the lateral extension (which is preferably thinner than the shaft and consequently causes less damage to the surrounding tissue than the shaft) is preferably positioned in the target region of tissue with less damage to the target region. In other words, in this simulated comparison, the neural interface system with an edge array preferably has a substantially smaller effective width, and results in a substantially smaller area of damage ($A_d$) than the exemplary planar array neural device (FIGS. 11D and 11E) or the exemplary microwire neural device (FIG. 11E).

As a person skilled in the art will recognize from the previous detailed description and from the figures and claims, modifications and changes can be made to the preferred embodiments of the invention without departing from the scope of this invention defined in the following claims.

What is claimed is:

1. A neural interface system, comprising:
   a) a substrate, comprising:
      i) a substantially cylindrical shaft formed as a rolled portion of the substrate; and
      ii) a lateral extension portion of the substrate, wherein the lateral extension extends longitudinally from at least a portion of the shaft and has a thickness less than a diameter of the shaft; and
   b) an electrode array, at least partially arranged on the lateral extension and radially offset from the shaft, wherein the electrode array comprises a plurality of electrode sites that are configured to electrically interface with their surroundings.

2. The neural interface system of claim 1, wherein the lateral extension is a trailing end of the rolled substrate.

3. The neural interface system of claim 1, wherein the lateral extension is tangent to the shaft.

4. The neural interface system of claim 1, wherein the rolled substrate defines a lumen.

5. The neural interface system of claim 4, wherein the lumen is configured to receive and transport a fluid.

6. The neural interface system of claim 4, further comprising a stylet insertable into the lumen.

7. The neural interface system of claim 6, wherein the stylet includes a microwire that functions as a single channel microelectrode.

8. The neural interface system of claim 5, further comprising an optical light source disposed within the lumen.

9. The neural interface system of claim 1, wherein the substrate has conductive traces coupled to the electrode array, and wherein the neural interface system further comprises a first electrical subsystem in electrical communication with the conductive traces.

10. The neural interface system of claim 9, wherein the conductive traces extend from the electrode array to a bond pad region of the substrate, and wherein the first electrical subsystem is coupled to the bond pad region of the substrate.

11. The neural interface system of claim 9, wherein the shaft defines a lumen with the first electrical subsystem being at least partially disposed within the lumen, and wherein the system further comprising a second electrical subsystem disposed outside the lumen and in direct electrical communication with the first electrical subsystem.

12. The neural interface system of claim 11, wherein the first electrical subsystem includes an amplifier at least partially disposed within the lumen.

13. The neural interface system of claim 11, wherein the first electrical subsystem includes a multiplexer at least partially disposed within the lumen.

14. The neural interface system of claim 1, wherein the substrate has conductive traces electrically coupled from the electrode array to a first electrical subsystem, and wherein a wired connector couples the first electrical subsystem to a second electrical subsystem.

15. The neural interface system of claim 1, wherein the substrate has conductive traces electrically coupled from the electrode array to a first electrical subsystem, and wherein the first electrical subsystem is configured to wirelessly communicate with a second electrical subsystem.

16. The neural interface system of claim 1, wherein the lateral extension has a slanted distal edge extending to a sharpened distal end of the shaft.

17. The neural interface system of claim 1, wherein the electrode array is arranged at least partially along a longitudinal edge of the lateral extension.

18. The neural interface system of claim 17, wherein the electrode array comprises at least one of a recording electrode site and a stimulation electrode site.

19. The neural interface system of claim 1, wherein the substrate is a polymer substrate having three metallization layers interspersed with silicon carbide insulation layers.

20. The neural interface system of claim 19, wherein the metallization layers are from about 0.7 μm to 1.3 μm thick.

21. The neural interface system of claim 1, wherein the lateral extension is coupled to the shaft by at least one rib bridging the lateral extension and shaft.

22. The neural interface system of claim 21, wherein the lateral extension is coupled to the shaft by at least two bridging ribs, thereby forming a perforated framework between the shaft and lateral extension with at least one opening bounded by the ribs.

23. A neural interface system, comprising:
  a) a polymer substrate, comprising:
    i) a substantially cylindrical shaft formed as a rolled portion of the substrate, wherein the cylindrical shaft defines a lumen; and
    ii) a lateral extension portion of the polymer substrate, wherein the lateral extension is tangent to the cylindrical shaft, and wherein the lateral extension has a thickness equal to or less than approximately 5 micrometers; and
  b) a high-density electrode array, linearly arranged along a longitudinal edge of the lateral extension and radially offset from the shaft, wherein the electrode array comprises at least one hundred microelectrode sites that are configured to electrically interface with their surroundings.

* * * * *